United States Patent [19]

Edgren et al.

[11] Patent Number: 5,006,346
[45] Date of Patent: Apr. 9, 1991

[54] DELIVERY SYSTEM

[75] Inventors: David E. Edgren, El Granada; Felix Theeuwes, Los Altos, both of Calif.

[73] Assignee: Alza Corporation, Palo Alto, Calif.

[21] Appl. No.: 350,482

[22] Filed: May 11, 1989

Related U.S. Application Data

[62] Division of Ser. No. 187,621, Apr. 28, 1988, Pat. No. 4,931,285.

[51] Int. Cl.$^5$ ............................................. A61K 9/24
[52] U.S. Cl. ...................................... 424/473; 427/3; 424/468
[58] Field of Search ............... 424/473, 468, 469, 472; 427/3, 214

[56] References Cited

U.S. PATENT DOCUMENTS

| | | | |
|---|---|---|---|
| 2,779,241 | 1/1957 | Howard | 89/1 |
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 4,002,173 | 1/1977 | Manning | 128/296 |
| 4,063,064 | 12/1977 | Saunders et al. | 219/121 L |
| 4,088,864 | 5/1978 | Theeuwes et al. | 219/121 LM |
| 4,160,020 | 7/1979 | Ayer et al. | 424/15 |
| 4,200,098 | 4/1980 | Ayer et al. | 128/260 |
| 4,207,893 | 6/1980 | Michaels | 128/260 |
| 4,285,987 | 8/1981 | Ayer et al. | 427/3 |
| 4,327,725 | 5/1982 | Cortese et al. | 128/260 |
| 4,716,041 | 12/1987 | Kjornaes et al. | 427/3 |
| 4,786,505 | 11/1988 | Lovgren et al. | 424/468 |
| 4,816,264 | 3/1989 | Phillips et al. | 424/468 |
| 4,853,230 | 8/1989 | Lovgren et al. | 424/468 |

*Primary Examiner*—Thurman K. Page
*Assistant Examiner*—Leon R. Horne
*Attorney, Agent, or Firm*—Paul L. Sabatine; Edward L. Mandell; Steven F. Stone

[57] ABSTRACT

A dosage form is disclosed comprising a coat that surrounds a drug. The coat comprises a subcoat and an overcoat thermally annealed to provide a single unit coat around the drug.

1 Claim, 2 Drawing Sheets

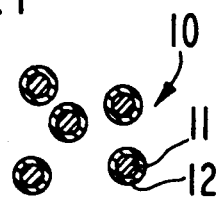
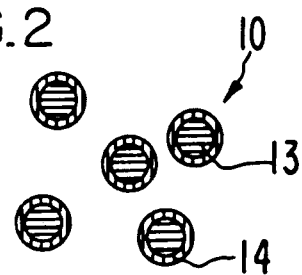
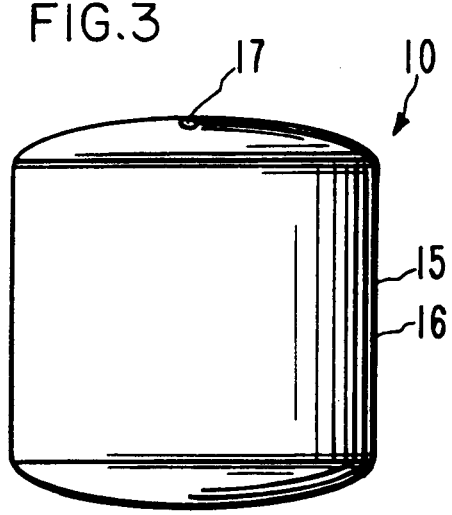
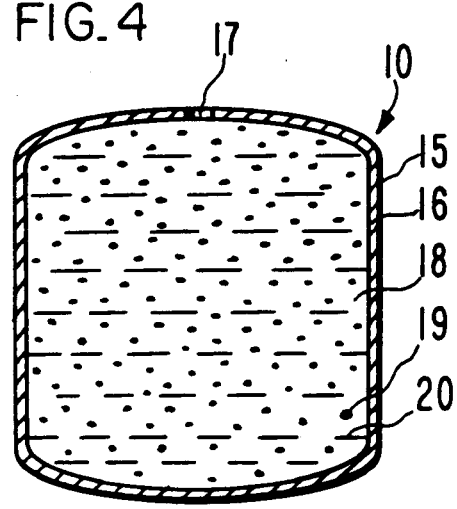
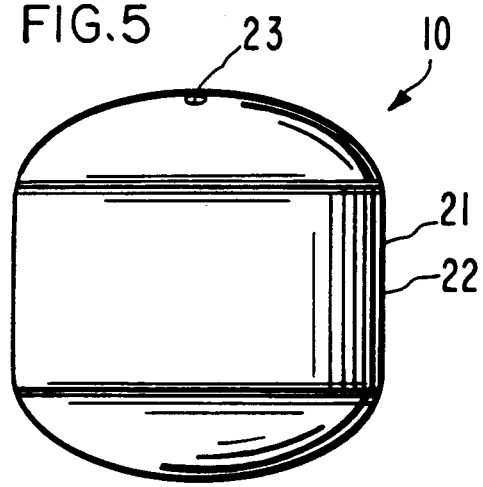
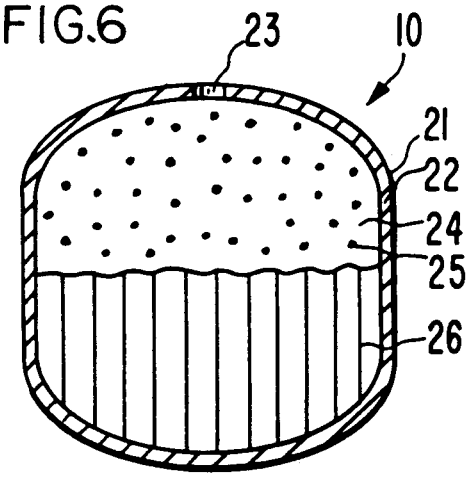

FIG_7
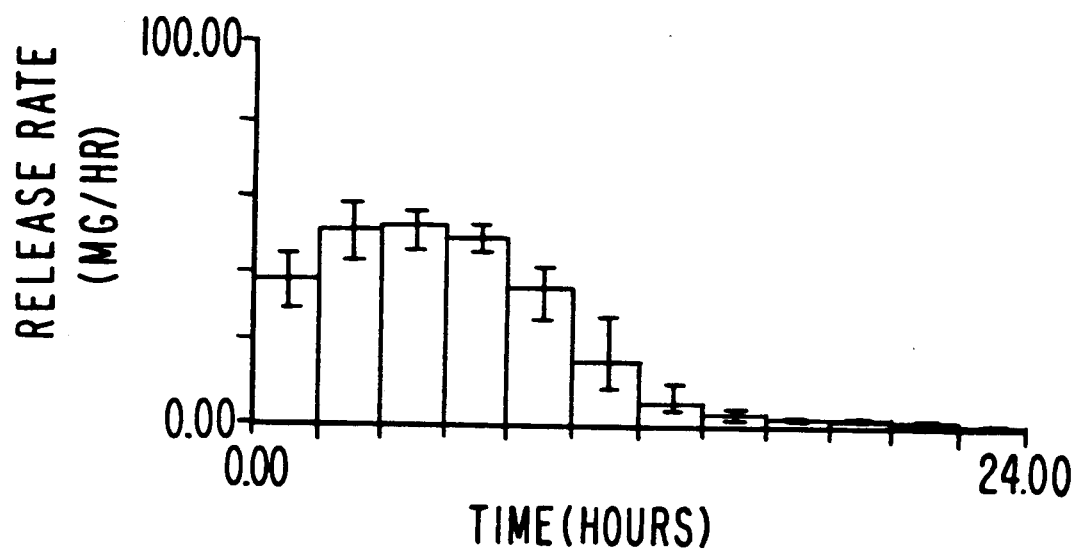
FIG.8
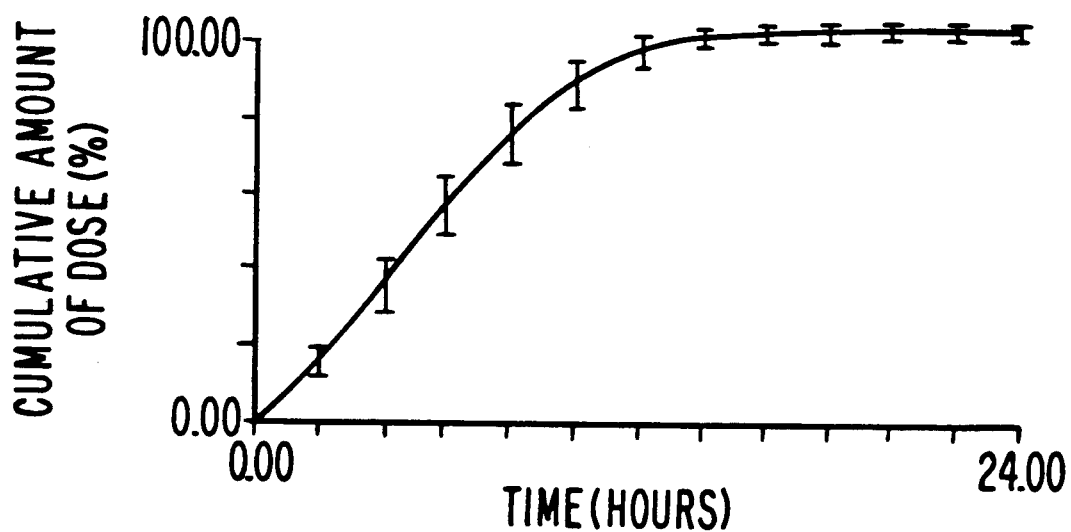

DELIVERY SYSTEM

CROSS-REFERENCE TO RELATED APPLICATIONS

This application is a division of U.S. patent appln. Ser. No. 07/187,621 filed Apr. 28, 1988, U.S. Pat. No. 4,931,285 which appln. is incorporated herein by reference and benefit is claimed of its filing date. These applications are assigned of record to ALZA Corporation of Palo Alto, Calif.

FIELD OF THE INVENTION

This invention pertains to both a novel and useful pharmaceutical coating composition. More particularly, the invention relates to a pharmaceutically acceptable coating composition o dosage forms such as delivery devices comprising a core comprising a therapeutically active drug; osmotic delivery systems; tablets; capsules; powders; granules, and beads.

BACKGROUND OF THE INVENTION

In Remington's *Pharmaceutical Sciences*, 14th Ed., p 1681, published in 1970, it is reported that pill coating has been a pharmaceutical technique for well over ten centuries. For example, Rhazes (850–932 A.D.) used a mucilage for coating pills in the ninth century, and Avicenna (980–1037 A.D.) is credited with the introduction of silver and gold pill coatings into medicine. The coating of pills with finely powdered talcum, called pearl coating, was popular at one time. Gelatin coating of pills was introduced by Garot in 1838. The first sugar-coated pills in the United States were imported from France in about 1842. The first sugar-coated pill was manufactured in the United States in 1956 by Warner, a Philadelphia pharmacist. The coating of pills with tolu was done in about 1860 and twenty-four year later Unna introduced enteric coated pills.

Various pharmaceutically indicated articles of manufacture have been coated by the drug dispensing art. For example, tablets were coated to provide a more attractive dosage form, to protect its drug content from moisture and to enhance its taste. Then too, tablets were provided with a coat for releasing a drug by enteric dissolution in the intestine of a warm-blooded animal. Recently osmotic dosage forms were coated with a semipermeable rate controlling wall for delivering a drug at a known rate per unit time.

While the above mentioned dosage forms are useful in the management of health and disease, serious disadvantages are associated with them. That is, usually organic solvents are used for applying the coating to the drug and drawbacks accompany the use of organic solvents. For example, organic solvents generally are toxic and they must be substantially driven from the dosage form to avoid a hazard to the dosage form's recipient. Another drawback is organic solvents are flammable thereby possibly providing the danger of fire to the manufacturer. Also, organic solvents present an environmental problem and they require complicated recovery systems to avoid contaminating the environment, which systems are expensive to operate. It will be appreciated by those skilled in the drug dispensing art that if a coating is provided that is substantially-free of organic solvents for coating drugs, drug granules, drug powders, and the like, such a coating would have an immediate positive value and, concomitantly, represent an advancement in the drug coating art. Likewise, it will be appreciated by those versed in the dispensing art that if a delivery device is made available comprising a coating applied from a nonorganic solvent, and which delivery device possesses the thermodynamic ability to deliver a beneficial drug at a controlled rate, such a delivery device would have a practical application in the fields of human and veterinary medicine.

OBJECTS OF THE INVENTION

Accordingly, in view of the above presentation, it is an immediate object of this invention to provide a novel and useful coating composition for dosage forms and which coating overcomes the disadvantages associated with the prior art.

Another object of this invention is to provide a new coating composition comprising pharmaceutically acceptable ingredients, and which coating composition is innocuous and useful for manufacturing dosage forms.

Another object of this invention is to provide a non-toxic coating composition free of organic solvents and which coating composition is useful for making dosage forms by standard manufacturing techniques.

Another object of the invention is to provide an aqueous coating composition which is relatively uncomplicated, capable of application without difficulty, and is applied at a relatively low cost.

Another object of the invention is to provide an aqueous polymeric coating that exhibits stability and resistance to sedimentation.

Another object of the invention is to provide an aqueous coating composition useful for manufacturing a drug delivery device possessing drug release rate controlling properties.

Another object of this invention is to provide a drug delivery device that can be manufactured by standard manufacturing techniques into various sizes, shapes and forms that comprise an improvement in the dispensing art, which comprises a non-toxic, aqueous coated wall that surrounds a drug.

Another object of this invention is to provide an aqueous-solvent coating composition that is non-flammable and is not an environmental hazard during formulation and not a hazard when applied to a drug core.

Another object of the invention is to provide a novel coating composition comprising a water carrier useful for coating a drug.

Other objects, features and advantages of this invention will be more apparent to those versed in the dispensing art from the following detailed specification taken in conjunction with the drawings and the accompanying claims.

BRIEF DESCRIPTION OF THE DRAWINGS

In the drawing figures, which are not drawn to scale but are set forth to illustrate various embodiments of the invention, the drawing figures are as follows:

FIG. 1 is an opened view depicting a powdered drug coated with the coating composition provided by this invention;

FIG. 2 is an opened view illustrating granules of a beneficial drug coated with a coating composition provided by this invention;

FIG. 3 is a view of an osmotic device designed and shaped for orally administering a beneficial drug to the gastrointestinal tract;

FIG. 4 is an opened view of the osmotic device of FIG. 3 depicting the wall of the osmotic device comprising the wall-forming coating composition of this invention;

FIG. 5 is a view of another embodiment of an osmotic device provided by this invention, which osmotic device is adapted and sized for oral admittance into the gastrointestinal tract of a host;

FIG. 6 is an opened view of the osmotic system of FIG. 5 for illustrating a wall formed from the coating composition provided by this invention;

FIG. 7 is a graph that depicts the drug delivery rate per unit time from a device comprising a wall coated by the process of the invention; and, FIG. 8 is a graph that depicts the cumulative amount of drug released per unit time by the delivery device of FIG. 7.

In the drawings and in the specification like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Turning now to the drawing figures in detail, which figures are examples of a dosage form comprising a coating composition provided by this invention and which examples are not to be considered as limiting the invention, one example of a dosage form is illustrated in FIG. 1. In FIG. 1, a dosage form 10 is seen in opened section. Dosage form 10 comprises a powdered drug 11, generally exhibiting a powder size that passes through a sieve having an opening of from 0.074 mm to 0.250 mm, surrounded by coating composition 12. Coating composition 12 comprises a subcoat and an overcoat. The subcoat comprises a finely divided membrane forming polymer dispersed in an oil-in-water emulsion, wherein the oil, generally present as an oily plasticizer, lowers the glass transition temperature of the membrane forming polymer. The overcoat comprises a water soluble composition wherein the glass transition temperature of the overcoat is higher than that of the subcoat. The subcoat and the overcoat are annealed, with the subcoat forming an insoluble membrane that surrounds powdered drug 11. The annealed overcoat forms a membrane that dissolves in an aqueous environment of use, leaving a continuous, insoluble membrane coating 12.

In FIG. 2, another embodiment of dosage form 10 is seen in opened view. In FIG. 2 dosage form 10 comprises granules of drug 13. The drug granules generally exhibit a granule size that passes through a sieve having an opening from greater than 0.250 mm to 9.50 mm. Drug granules 13 are surrounded by aqueous-applied coating composition 14. Coating composition 14 is applied in two steps, first a subcoat followed by an overcoat. The two coats are annealed, which annealing process coalesces the polymer in the subcoat thereby providing a continuous membrane or film. The overcoat protects the subcoat during the annealing process and the overcoat additionally prevents the subcoat of one dosage form from fusing with the subcoat of a neighboring dosage form.

In FIG. 3, another embodiment of dosage form 10 is illustrated manufactured as an osmotic drug delivery device. In FIG. 3 osmotic dosage form 10 comprises a body 15 comprising a wall 16 that surrounds and forms an internal compartment, not seen in FIG. 3. Osmotic dosage form 10 comprises at least one passageway 17 for connecting the interior of osmotic dosage form 10 with the exterior of osmotic dosage form 10 when in a biological environment of use.

In FIG. 4 osmotic dosage form 10 of FIG. 3 is seen in opened view. In FIG. 4 osmotic dosage form 10 comprises body member 15, aqueous coated wall 16 and exit passageway 17. Wall 16 surrounds and forms an internal compartment 18. Internal compartment 18 comprises a dispensable drug 19, represented by dots, and an optional osmagent, represented by dashes. Wall 16 is permeable to the passage of an exterior fluid present in the environment of use, and wall 16 is substantially impermeable to the passage of drug 19 and osmagent 20.

In FIG. 5 another embodiment of dosage form 10 is illustrated and made as an osmotic drug delivery device. In FIG. 5 osmotic dosage form 10 comprises a body member 21 comprising a wall 22 that surrounds and forms an internal compartment, not seen in FIG. 5. Dosage form 10 comprises at least one passageway 23, formed during the manufacture of dosage form 10 or, optionally, formed when dosage form 10 is in a fluid environment of use. Passageway 23 connects the interior of dosage form 10 with its exterior for delivering a drug to an environment of use.

In FIG. 6 dosage form 10 of FIG. 5 is seen in opened view. In FIG. 6 dosage form 10 comprises body member 21, aqueous coated annealed wall 22 and exit passageway 23. Wall 22 surrounds, forms and defines an internal compartment 24. Internal compartment 24 comprises a first composition identified by dots 25, and a second composition 26 identified by vertical lines. First composition 25 comprises a beneficial drug and second composition 26 comprises an expandable hydrogel. First composition 25 and second composition 26 are in laminar arrangement and they cooperate with wall 22 for the effective delivery of a drug through exit passageway 23 to an environment of use.

FIG. 7 and FIG. 8 exemplify the release of an active agent from a delivery system made according to this invention. The release rate per unit time and the cumulative amount release of the drug potassium chloride are depicted, respectively, for a delivery system made according to this invention.

While FIGS. 1 through 8 illustrate different embodiments of dosage forms that can be coated with the coating composition of this invention, it is to be understood that the coating composition can be applied to a wide variety of dosage forms, which dosage forms comprise various shapes, sizes and forms. The coating composition can be applied to devices not limited to but including uses for buccal, implant, artificial gland, cervical, intrauterine, nose, and the like. In these forms the device coated with the coat of this invention can be adapted for administering a beneficial medicine to animals, warm-blooded mammals, humans, farm and zoo animals, avians and reptiles.

DETAILED DESCRIPTION OF THE INVENTION

In accordance with the practice of this invention a drug or the like is first coated with a subcoat followed by an overcoat. The subcoat comprises a membrane forming polymer, a plasticizer, an emulsifier, an optional hydrophilic enhancer, and an aqueous carrier. The overcoat comprises a membrane or film forming polymer, an optional plasticizer and an optional carrier. The polymeric material used for forming the subcoat, which subcoat when the dosage form is in operation in a fluid environment of use, comprises the sole coat on the form and is a polymer that is nontoxic and does not adversely affect a beneficial drug and an animal host, including humans. In a presently preferred embodiment, polymeric materials useful for providing the subcoat comprise polymeric members selected from the group consisting of a cellulose ester, cellulose ether, cellulose ester-ether, cellulose acylate, cellulose diacylate, cellulose triacylate, cellulose acetate, cellulose diacetate and cellulose triacetate. More specific examples of polymeric materials comprise a member selected from the group consisting of cellulose acetaldehyde methyl carbamate, cellulose acetate succinate, cellulose acetate dimethylaminoacetate, cellulose acetate ethylcarbamate, cellulose acetate dipalmate, cellulose acetate dioctanoate, cellulose acetate dicaprylate, cellulose acetate pentylate, cellulose acetate valerate, cellulose acetate succinate, cellulose acetate propionate, cellulose acetate p-toluene sulfonate, cellulose acetate butyrate, cellulose propionate butyrate, and the like. Generally the polymer used for forming the composition will have a particle size of less than about 2 to 15 microns and more, preferably less than about 2 to 10 microns. The amount of polymer on a weight basis of the coating in a final, dry coated dosage form generally is about 15 to 95%.

The subcoating additionally comprises a non-toxic plasticizer or blends of plasticizers. The plasticizers presently preferred are highboiling softening agents, which are often liquids, pastes, or waxes at room temperature, that are added to the subcoat composition to facilitate processing, and to increase flexibility and toughness. The plasticizers generally comprise, in a presently preferred embodiment, a member selected from the group consisting of monoglycerides, diglycerides, triglycerides, alkyl phthalyl alkyl glycolates, trialkyl esters of acyl citric acid, dialkyl adipates, dialkyl phthalates, dialkyl sebacates, fatty acid ester derivatives, akyl-aryl phosphates, fatty acid esters of polysaccharides, triethyl citrate, acetyltriethyl citrate, diethyl phthalate, diethyl tartrate, dibutyl phthalate, dibutyl sebacate, dibutyl tartrate, dibutyl maleate, dibutyl succinate, diethyl succinate, propylene glycol, glycerin, monoacetin, diacetin, triacetin, polyethylene glycol, di(methoxyethyl) phthalate, methyl and ethyl phthalate ethyl glycolate, butyl phthalyl butyl glycolate, benzyl phthalate, ethylene glycol diacetate, methylglycol phthalate, ethylene glycol monoacetate, trimethyl phosphate, triethyl phosphate, dioctyl adipate, dioctyl phthalate, dibutyloxyethyl phthalate, epoxidized natural glyceride of unsaturated fatty acids, soybean oil epoxide, di-n-hexyl azelate, dimethyl phthalate, diphenyl phthalate butyl stearate, diethyl oxalate, diisodecyl adipate, dicyclohexyl phthalate, di(2-ethylhexyl) adipate, cresyldiphenyl phosphate, tributyl citrate, acetyl tributyl citrate, trimethyl citrate, acetyltri-n-hexyl citrate, n-butyryltri-n-hexyl citrate, tricyclohexyl citrate, acetyltri-n-(hexyl/octyl/decyl) citrate, acetyltri-n-(octyl/decyl) citrate, acetyltri-n-(decyl/dodecyl)citrate, tristearyl citrate, stearyl citrate-mono, methylglycol stearate, butyl phthalyl butyl glycolate, tri(n-octyl/n-decyl) trimellitate, triisodecyl trimellitate, tri-n-hexyl trimellitate, di(2-ethylhexyl) isophthalate, butyl ricinoleate, polymeric plasticizer acetylated, citric acid esters, natural oils and derivatives of natural oils, fish oils, lard oils, vegetable oils, babassu oil, castor oil, coconut oil, cottonseed oil, corn oil, linseed oil, olive oil, palm oil, peanut oil, safflower oil, sesame oil, soybean oil, tall oil, acetyl tri-2-ethylhexyl citrate, linoleic acid, oleic acid, butyl stearate, benzyl benzoate, polysiloxanes, silcone oils, mineral oils, hydrogenated oils, methyl ester of rosin, stearic acid, cetyl alcohol, acetylated glycerides, glycerol esters, polyethylene glycol, and the like. The amount of plasticizing agent in a final subcoat on a drug delivery dosage form is about 2% to 75%.

The subcoat comprises also an emulsifying agent or blends of emulsifying agents. The emulsifying agents generally are surface active agents comprising anionic, polar, nonpolar, nonionic, amphoteric, zwitterionic and cationic active emulsifying agents. The amount of emulsifying agents in an aqueous coating composition usually is about 0.1% to 20%, and more preferably about 0.01% to 4%, by weight, of water in the aqueous phase. Representatives of general classes of emulsifying agents comprise a member selected from the group consisting essentially of alkanolmides, alkyl sulfonates, amines and amides sulfonated, betaine emulsifiers, diphenyl sulfonates, ethoxylated alcohols, ethoxylated alkyl phenols, ethoxylated amines, ethoxylated amides, ethoxylated fatty acids and oils, fatty esters, florocarbons, glycerl esters, glycol esters, heterocyclic emulsifiers, isethionates, lanolin based emulsifiers, lecithin based emulsifiers, phospholipids, lignin emulsifiers, monoglycerides, olefin sulfonates, phosphate emulsifiers, phosphate esters emulsifiers, polyamino carboxylic emulsifiers, protein emulsifiers, quaternary emulsifiers, sarcosine emulsifiers, silicone emulsifiers, siloxane emulsifiers, sorbitan emulsifiers, sulfo succinate emulsifiers, sucrose esters, ethoxylated alcohol sulfates, ethoxylated alcohol sulfates, sulfates and sulfonates of ethoxylated alkyl phenols, sulfates of fatty acids, sulfates of oils, sulfonates of oils, sulfates of fatty acids, sulfonates of fatty acids, sulfonates of alkyl aryls, sulfonates of naphtholenes, sulfonates of dodecyl and tridecylbenzenes, sulfonates of petroleum, tridecyl and dodecyl benezene sulfonic acids, taurates, tertiary amine oxides, and thio and mercapto emulsifiers. Representatives of nonionic emulsifying agents include polyoxyethylene sorbitan tristearate, polyoxyethylene sorbitan mono-oleate, polyoxyethylene sorbitan monopalmitate, sorbitan monopalmitate, polyoxyethylene sorbitan tri-oleate, polyoxyethylene sorbitan monostearate, polyoxyethylene alkyl phenol, polyoxyethylene sorbitan monolaurate, polyoxyethylene oxypropylene stearate, glycerol monostearate, propylene glycol fatty acid ester, and the like. Representatives of anionic emulsifying agents include triethanolamine oleate, sodium oleate, calcium stearoxyl-2-lactylate, calcium dodecylbenzene sulfonate, ammonium lauryl sulfate, sodium alkyl sulfate, triethanolamine lauryl sulfate, sodium dodecylsolfate, and the like. Exemplary cationic emulsifiers include high molecular weight fatty amine blends, polyoxyethylene fatty amines, polyoxyethylene tallow amines, N-cetyl-N-ethyl morpholinium ethyl sulfate, and the like. The emulsifiers are known in *McCutcheon's Detergents and Emulsifiers*, North American Edition (1979) and International Edition (1979), in the *Encyclopedia of Chemical Technology*, by Kirk-Othmer, 3rd Ed. Vol. 8, pp 900-30, (1984), and in the *Cosmetic, Toiletry, and Fragrance Association Cosmetic Ingredient Dictionary* 3rd Ed., (1982) and 3rd Ed., Supplement (1985).

The subcoat comprises an optional hydrophilic enhancer or blends of hydrophilic enhancers that aid in transporting fluid from the environment of use into a dosage form. The hydrophilic enhancers in one embodiment are polyhydric alcohols and derivatives thereof, such as polyalkylene glycols of the formula H-(O-alkylene)$_n$OH, wherein the bivalent alkylene radical is a straight or branched chain of from 1 to 10 carbons and n is 1 to 500 or higher. Typical glycols comprise polyethylene glycols 300, 400, 600, 1500, 3350, 4000 and 6000 of the formulae H(OCH$_2$CH$_2$)$_n$OH wherein n is, respectively, 5 to 5.7, 8.2 to 9.1, 12.5 to 13.9, 29 to 36, 29.8 to 37, 68 to 84, and 158 to 204. Other polyglycols comprise the low molecular weight glycols such as polypropylene glycol, polybutylene glycol and polyamylene glycol. Other hydrophilic enhancers include polyvinyl pyrrolidone, hydroxypropyl methylcellulose, hydroxypropyl cellulose, sorbitol, fructose, mannitol, citric acid, sodium citrate or entirely active materials such as finely divided cellulose acette trimellitate, cellulose acetate phthalate, hydroxypropyl methylcellulose phthalate, acrylic copolymers, polyvinyl acetae phthalate. The amount of hydrophilic enhancer in the aqueous emulsion is 0% to 70%, with water and the concentration of oil ingredients in the aqueous coating composition equal to 100%. Hydrophilic enhancers are known in U.S. Pat. No. 4,160,020.

The overcoat annealing composition comprises a water soluble polymer such as, in a presently preferred manufacture, a member selected from the group consisting of hydroxypropyl cellulose, methyl cellulose, methylethyl cellulose, polyvinylpyrrolidone, sodium carboxymethylcellulose, hydroxypropylmethyl cellulose, and the like. Other optional annealing agents comprise gums such as pectin, acacia, tragacanth, karaya, locust, bean gum, chondrus and alginic acid. The overcoat can comprise from 10% to 100% of the final dosage form when applied by compression coating. In an optional embodiment the overcoat can comprise from 0% to 60% of a plasticizer such as glycerin, propylene glycol glyceryl triacetate, polyethylene glycol, and the like, and water to 100%. The overcoat comprising the water soluble ingredients can be coated by spraying, dipping, and the like. The overcoat and the subcoat are annealed in a presently preferred embodiment at about 35° C. to 65° C., for 10 to 72 hours in a forced air oven. As an option the annealing process can result in causing the plasticizer in the overcoat to partition from the overcoat into the subcoat. The subcoat, overcoat, or both subcoat and overcoats can, optionally, contain finely divided insoluble material. These are useful for reducing tackiness or for enhancing mechanical integrity of the layers. Typical materials for this application wold be microcrystalline cellulose, titanium dioxide or fumed silicon dioxide.

The expression, "exit passageway," as used herein for a drug delivery device coated with the composition of this invention, comprises means and methods suitable for the controlled, metered release of a drug from a drug delivery device or dosage form. The exit means comprise at least one passageway, orifice, or the like, through the wall of the dosage form. The expression, "at least one passageway," embraces aperature, orifice, bore, pore, porous element, and the like, through which pores a drug can travel, hollow fiber, capillary tube, porous overlay, porous insert, and the like. The expression also includes a material that erodes, or is leached from a wall in a fluid environment of use to produce at least one passageway of controlled releasing dimensions. Representative materials for forming a passageway or two passageways, or a multiplicity of passageways in an environment of use include an erodible, innocuous poly(glycolic) acid, or poly(lactic) acid member in the wall; a gelatinous filament; a particle of polyvinyl alcohol; leachable materials such as a fluid removable pore forming polysaccharide, salt, oxide, polyhydric alcohols, and the like. A passageway or a plurality of passageways of governed dimensions for the controlled release of a drug can be formed by leaching a passageway former such as sorbitol from a wall. The passageway can have any shape such as round, triangular, square, elliptical, irregular, and the like, for assisting in the metered release of a drug from a dosage form. A dosage form can comprise one or more than one passageways in spaced apart relations or, optionally, on more than a single surface of a dosage form. Passageways and equipments for forming passageways are disclosed in U.S. Pat. Nos. 3,845,770; 3,916,889; 4,063,064; and 4,088,864. Representative passageways formed by the governed leaching of a pore former to produce a pore of precontrolled rate releasing size are disclosed in U.S. Pat. Nos. 4,200,098 and 4,285,987.

The expression, "therapeutically active drug," as used herein, denotes a beneficial medicine neat, or a composition comprising a beneficial drug and other composition forming ingredients. In the specification and the accompanying claims the terms, "medicine and drugs," are used as equivalents, and the term, "drug," includes any physiologically or pharmacologically active substance that produces a local or a systemic effect in animals, including warm-blooded mammals, primates and humans. The terms, "physiologically and pharmacologically," are defined in *Stedman's Medical Dictionary*, published by Williams and Wilkins, (1966), Baltimore, Md. The active drug that can be coated with a composition provided by this invention includes inorganic and organic drugs, without limitations, comprising drugs that act on the central nervous system, depressants, hypnotics, sedatives, psychic energizers, tranquilizers, anticonvulsants, muscle relaxants, anti-Parkinsons, analgesics, anti-inflammatories, local anesthetics, muscle contractants, antimicrobials, antimalerials, hormones, contraceptives, sympathomimetics, diuretics, antiparasitics, neoplastics, hypoglycemics, ophthalmics, electrolytes, and cardiovascular drugs. These drugs and their daily dosage are known in the art in *Pharmaceutical Sciences*, by Remington, 16th Ed., (1980), published by Mack Publishing Co., Easton, Pa.

The drug can be in various pharmaceutically acceptable forms, such as uncharged molecules, molecular complexes, pharmacologically acceptable salts such as hydrochloride, hydrobromide, sulfate, laurylate, palmitate, phosphate, nitrate, borate, acetate, maleate, tartrate, oleate and salicylate. For acidic medicines salts of metals, amines or organic cations; for example quaternary ammonium can be used. Derivatives of medicines, such as an ester, ether and amides, can be used. Also, a medicine that is water insoluble can be used in a form that is a water soluble derivative thereof to serve as a solute, and on its release from a dosage form it is converted by enzymes, hydrolyzed by the body pH, or other metabolic process to the original biologically active form.

Hydrophilic polymers that exhibit an osmotic pressure gradient, imbibe fluid and expand, that are useful for manufacturing as coated osmotic dosage forms comprise noncross-linked hydrogels, and lightly cross-linked hydrogels, such as cross-linked by covalent or ionic bonds. The hydrophilic hydrogels usually exhibit a 2 to 50 fold volume increase comprising acidic carboxy polymer having a molecular weight of 450,000 to 4,000,000; poly(hydroxyalkyl methacrylate) having a molecular weight of 30,000 to 5,000,000; poly(vinylpyrrolidone) having a molecular weight of 10,000 to 360,000; polyacrylic acid having a molecular weight of 80,000 to 200,000; polyethylene oxide polymers having a molecular weight of 100,000 to 5,000,000, sodium salt of carboxymethyl cellulose cross-linked, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; U.S. Pat. No. 4,327,725 issued to Cortese et al; and in the *Handbook of Common Polymers,* by Scott and Roff, published by Chemical Rubber Co., Cleveland, Ohio.

The osmagent optionally present in an osmotic dosage form coated according to the mode and the manner of the invention comprise magnesium sulfate, magnesium chloride, sodium chloride, lithium chloride, potassium sulfate, sodium carbonate, sodium sulfite, lithium sulfate, potassium chloride, sodium sulfate, mannitol, urea, sorbitol, inositol, raffinose, fructose, sucrose, glucose, and the like. The osmagents are known in U.S. Pat. No. 4,327,725.

The coating composition can be applied to a drug core by standard manufacturing techniques. For example, one manufacturing procedure is the air suspension technique. The air suspension procedure consists in suspending and tumbling the drug core to be coated in a current of air and the coating composition until a coat is applied to the drug core. Air suspension procedures are known in U.S. Pat. No. 2,799,241; in *J. Am. Pharm. Assoc.,* Vol. 48, pp 451–59; (1959), and ibid, Vol. 49, pp 82–4, (1960). Drug cores can be coated with a coating composition in a Wurster ® air suspension coater or in an Aeromatic ® air suspension coater. Other coating procedures such as pan coating can be used for applying a subcoat or an overcoat. Generally the subcoat will be about 2 to 20 mils, usually 3 to 10 mils, thick and the overcoat will be about 1 to 12 mils and, more preferably, 1 to 6 mils thick. The polymers used to provide the subcoat can be milled in a vehicle of either gas or liquid to a fine particle size by using an impact mill, an air jet, a microfluidizer, an attrition mill, ball mill, cage mill, colloid mill, cone mill, grinding mill, hammer mill, and the like. Another technique that can be used to form finely divided polymers is to dissolve the polymer in an organic solvent, which is emulsified in water with a surfactant and then vacuum-off the solvent. For example, cellulose acetate comprising an acetyl content of 39.8% is dissolved in cyclohexanone with sodium lauryl sulfate and the mixture is emulsified in water with shear. The cyclohexanone then is drawn off under reduced pressure, leaving aqueous dispersion of finely divided cellulose acetate. This dispersed cellulose acetate is then coated according to the process of this invention. Another example comprises plasticizing a polymer such as ethyl cellulose, melting it and dispersing the melt in water with high shear and elevated temperature.

DETAILED DESCRIPTION OF THE EXAMPLES

The following examples are merely illustrative of the present invention and they should not be considered as limiting the scope of the invention in any way, as these examples and other equivalents thereof will become more apparent to those skilled in the drug delivery art in the light of the present disclosure, the drawings and the accompanying claims.

EXAMPLE 1

A drug delivery dosage form adapted, designed and shaped as an osmotic delivery system is manufactured as follows: first, 64 grams of cellulose acetate having an acetyl content of 39.8% was milled by dispersing it in 576 grams of water. This dispersion was passed five times through a microfluidizer to a particle size of about 5 microns. The slurry was added slowly into an emulsion comprising 86.4 g of triacetin, 9.6 g of polyoxyethylene-20-sorbitan tristearate, an emulsifier, in 2,464 ml of distilled water at 67° C. with vigorous stirring for 15 to 20 minutes. The emulsion was previously prepared by heating the water, emulsifier and the triacetin to 67° C. with stirring for 10 to 15 minutes. The resulting emulsified coating composition was stirred constantly while cooled slowly to room temperature over a 2 hour period.

The aqueous subcoat was coated onto 500 mg potassium chloride cores in an Aeromatic ® coater by spraying the coating at a fluid pump rate of 6 ml/min and at an inlet temperature of 37°–39° C., until about 4.5 mil thick coating was applied to each potassium core.

Next, the subcoated cores were overcoated with an overcoat comprising 20 g of hydroxypropylcellulose in 780 mil of distilled water using the Aeromatic coater. The overcoat was applied at a fluid pumping rate of 2 mil/min until a coating about 3 mil thick surrounded the subcoat.

EXAMPLE 2

The above procedure is followed to provide a subcoat comprising 50% cellulose acetate having an acetyl content of 39.8%, 44% triacetin and 6% polyoxyethylene sorbitan monolaurate, and an overcoat comprising 93% hydroxypropylcellulose, 6% polyethylene glycol 3350 and 1% titanium dioxide. The cellulose acetate was milled by passing it six times through an air jet mill until an average particle size of less than 20 microns was obtained. The milled powder was sprinkled slowly into an emulsion comprising 86.4 grams triacetin, 9.6 grams polyoxyethylene-20-tristearate and 3040 ml water, processed with the procedures detailed in Example 1, except that all mixing was done at ambient temperature. The coatings are annealed at 50° C. for 24 hours in a forced air oven.

EXAMPLE 3

A dosage form adapted, designed and shaped as an osmotic drug delivery system is manufactured as follows: first, a drug containing composition as expressed on a percentage basis of the final composition is prepared by passing through a 40 mesh screen 74.40 weight percent (wt %) polyethylene oxide having a molecular weight of 200,000 grams per mole. Then, 20.10 wt % of nifedipine and 5.00 wt % hydroxypropylmethylcellulose having an average molecular weight of 11,200 grams per mole is added to the polyethylene oxide and the three ingredients mixed for about 10 minutes in a conventional mixer. While the three ingredients are mixing, denatured, anhydrous ethanol is added q.s. slowly to the mixer and the mixing continued for an additional 5 minutes. The wet granulation is passed through a 20 mesh screen, dried at room temperature for 16 hours and passed again through a 20 mesh screen. Finally, 1.5 wt % of magnesium stearate is added to the granulation and all the ingredients mixed in a roller mill for 1 to 3 minutes.

A second composition is prepared by mixing 64.30 wt % of polyethylene oxide having a molecular weight of 5,000,000 grams per mole with 29.20 wt % sodium chloride and the mix is passed through a 40 mesh screen. Then, the just prepared mixture is mixed with 5.00 wt % hydroxypropylmethylcellulose having a number average molecular weight of 9,200 grams per mole and 1.00 wt % ferric oxide for 10 minutes in a mixer. Then, anhydrous ethanol q.s. is slowly added to the blending mixture and all the ingredients mixed for an additional 5 minutes. The freshly prepared wet granulation is passed through a 20 mesh screen, allowed to dry at room temperature for 16 hours, and again passed through a 20 mesh screen. The screened granulation is mixed with 0.50 wt % of magnesium stearate in a roller mill for 1 minute.

A drug core is prepared by adding 328 mg of the first composition to a tablet press and tamped, then 164 mg of the second composition is added to the press and the two compositions pressed into a two-layered drug core.

The compressed core is then coated with a subcoat comprising approximately 5 mils of 40 wt % cellulose acetate having an acetyl content of 39.8%, 50 wt % of triacetin, 4 wt % of polyvinyl pyrrolidone with average molecular weight of 40,000 grams per mole and 6 wt % of polyoxyethylene sorbitan tristearate. The subcoat is applied as described in Example 1.

An overcoat composition is prepared by mixing 70 wt % of hydroxypropylmethylcellulose having a molecular weight of 11,900 grams per mole with 30 wt % polyethylene glycol having a molecular weight of 3350. The overcoat is coated to a thickness of approximately 1 mil and the two coats annealed as described in Example 1. The final dosage form comprises 66 mg of drug. A 20 mil orifice is drilled through the two coats on the drug layer side. The dosage form, in an in vitro fluid environment, exhibited a mean release rate of 4.4 mg/hr.

EXAMPLE 3

The procedures set forth above were followed in the present example to provide the following dosage form: A dosage form comprising a first composition weighing 301 mg and comprising 4.0 wt % prazosin hydrochloride; 90.5 wt % of polyethylene oxide having a molecular weight of 90,000 grams per mole; 5.0 wt % hydroxypropylmethylcellulose having a molecular weight of 11,300 grams per mole; and 0.50 wt % magnesium stearate; a second composition in layered relation to the first composition, the second composition weighing 200 mg and comprising 64.5 wt % coagulated polyethylene oxide having a molecular weight of about 5,000,000; 29.0 wt % sodium chloride; 5.0 wt % hydroxypropylmethylcellulose having a molecular weight of 11,300 grams per mole; 1.0 wt % ferric oxide; and 0.50 wt % magnesium stearate. The compressed two-layered core is coated with a subcoat weighing 74.8 mg and comprising 40 wt % cellulose acetate having an acetyl content of 39.8%; 54 wt % triacetin and 6.0 wt % polyoxyethylene sorbitan tristearate. The overcoat weighs 10.5 mg and comprises 70 wt % hydroxypropylmethylcellulose having a molecular weight of 11,900 grams per mole, and 30 wt % of polyethylene glycol 3350. The dosage form comprises a 20 mil passageway on the drug layer side and exhibits a mean release rate of 0.74 mg/hr, with a nominal T-90 of 11 hours.

EXAMPLE 4

The procedures set forth above were followed in this example to provide a dosage form comprising: a drug core weighing 323.2 mg comprising 5.96 wt % salbutamol hemisulfate, 89.04 wt % sodium chloride, 2.0 wt % polyvinylpyrrolidone, 2.0 wt % cross-linked sodium carboxymethylcellulose and 1.0 wt % magnesium stearate; a subcoat comprising 40 wt % cellulose acetate having an acetyl content of 39.8%, 54 wt % triacetin and 3 wt % polyoxyethylene sorbitan mono-oleate and 3 wt % polyoxyethylene sorbitan monolaurate; and an overcoat comprising 35 wt % hydroxypropylmethylcellulose having a molecular weight of 11,900 grams per mole, 35 wt % hydroxypropylcellulose having a molecular weight of 73,000 grams per mole, and 30 wt % polyethylene glycol 3350. The dosage form was annealed as described previously. The dosage form had two 10 mil orifices positioned one on each side, a mean release rate of 1.0 mg/hr, and a nominal T-90 of 27 hrs.

EXAMPLE 5

The procedure set forth in Example 1 is followed with all the conditions as set forth, except that 32 grams of cellulose acetate having an acetyl content of 32% is mixed with 32 grams of cellulose acetate having an acetyl content of 39.8%, which blend is milled to a particle size of 10 microns.

EXAMPLE 6

The procedures described in the above examples were followed in this example to provide a delivery device with the following structure: (a) an osmotic core weighing 521 mg and comprising 94 wt % potassium chloride, 5 wt % polyvinyl pyrrolidone and 1 wt % magnesium stearate; (b) an annealed latex wall, which wall comprises: (i) a subcoat 2.4 mils thick, weighing 31.2 mg and comprising 38.1 wt % cellulose acetate having an acetyl content of 39.8%, 54 wt % triacetin, and 6 wt % Tween 65 and, (ii) an overcoat 3.4 mils thick, weighing 17.9 mg and comprising 70 wt % hydroxyproplymethylcellulose having a molecular weight of 11,900 and 30 wt % polyethylene glycol. The device had a 10 mil orifice, a collapse pressure of 104±11 mm Hg, an osmotic water permeability value, k, of $6.3 \times 10^{-4}$ cm mil/atm hr. The device was annealed 1 day at 45° C. in a forced air oven. The rate of release for the device is seen in FIG. 7 and the cumulative amount released is seen in FIG. 8.

An embodiment of the invention pertains to a method for administering a drug to the gastrointestinal tract to establish a drug blood level. The method comprises the steps of: (A) admitting into the gastrointestinal tract an osmotic dosage comprising: a wall comprising a nontoxic composition that is permeable to the passage of fluid and substantially impermeable to the passage of a drug; which wall surrounds and forms: (1) a compartment comprising a gastrointestinal administrable drug; and, (2) at least one exit passageway in the wall connecting the exterior of the dosage form with the interior of the dosage form; (B) imbibing fluid through the wall into the compartment at a rate determined by the permeability of the wall and the osmotic pressure gradient across the wall to form in the compartment a dispensable composition that is hydrodynamically and osmotically pumped from the dosage form through the passageway; (C) thereby delivering the drug in a therapeutically effective amount to the gastrointestinal tract for passing into the blood circulation for establishing a blood level over a prolonged period of time.

The invention pertains to an osmotic therapeutic system manufactured with an annealed wall for delivering a drug at a controlled rate over time. While there has been described and pointed out the novel features of the invention as applied to presently preferred embodiments, those skilled in the art will appreciate that various modifications, changes and omissions in the invention illustrated, described and claimed can be made without departing from the spirit of the invention.

We claim:

1. A therapeutic composition comprising:
   (a) a drug;
   (b) an oil-in-water subcoat comprising from 15% to 75% of a member selected from the group consisting of a cellulose ether, a cellulose ester and a cellulose ester-ether, an optical plasticizer and comprising from 0.1% to 20% of an emulsifying agent comprising a member selected from the group consisting of nonionic, anionic and cationic agents; and
   (c) an overcoat comprising a member selected from the group consisting of a hydroxypropylcellulose, hydroxypropylmethylcellulose, methylcellulose and carboxymethylcellulose, and an optional plasticizer, and wherein the subcoat and the overcoat are annealed at a temperature up to 65° C. for up to 72 hours to provide the therapeutic annealed composition comprising the drug.

* * * * *

UNITED STATES PATENT AND TRADEMARK OFFICE
CERTIFICATE OF CORRECTION

PATENT NO. : 5,006,346
DATED : April 9, 1991
INVENTOR(S) : David E. Edgren and Felix Theeuwes It is certified that error appears in the above-identified patent and that said Letters Patent is hereby corrected as shown below:

Claim 1, in column 14, in line 4, delete "optical" and insert ----optional----.

Signed and Sealed this

First Day of September, 1992

Attest:

DOUGLAS B. COMER

*Attesting Officer*  *Acting Commissioner of Patents and Trademarks*